United States Patent
Kostka et al.

(12) 
(10) Patent No.: US 6,375,969 B1
(45) Date of Patent: Apr. 23, 2002

(54) BROADCAST CARRIERS FOR PESTICIDES AND THEIR USE

(75) Inventors: Stanley J. Kostka, Cherry Hill; Rennan Pan, Plainsboro; Christopher M. Miller, Clementon, all of NJ (US); Norman Robert Pallas, Florissant, MO (US)

(73) Assignees: Rhodia Inc., Cranbury, NJ (US); Aquatrols Holding Co., Inc., Wilmington, DE (US)

( * ) Notice: Subject to any disclaimer, the term of this patent is extended or adjusted under 35 U.S.C. 154(b) by 0 days.

(21) Appl. No.: 09/347,999

(22) Filed: Jul. 6, 1999

Related U.S. Application Data

(63) Continuation-in-part of application No. 08/715,726, filed on Sep. 25, 1996, now abandoned.

(51) Int. Cl.$^7$ .................... A01N 25/08; A01N 25/14; C05C 9/00
(52) U.S. Cl. .............. 424/409; 71/11; 71/28; 252/363.5; 424/421; 504/367; 514/770; 514/919; 514/952
(58) Field of Search ............ 252/363.5; 423/335; 71/11, 31, 28; 424/408, 409, 421; 504/187, 367; 514/770, 772.4, 777, 919, 952; 516/79

(56) References Cited

U.S. PATENT DOCUMENTS

| | | | |
|---|---|---|---|
| 2,396,278 A | | 3/1946 | Lind |
| 2,486,921 A | | 11/1949 | Byerly |
| 2,486,922 A | | 11/1949 | Strain |
| 3,137,618 A | * | 6/1964 | Pearce .................. 424/421 |
| 4,144,050 A | * | 3/1979 | Frensch et al. ......... 424/421 X |
| 4,857,101 A | | 8/1989 | Musco et al. ............. 71/94 |
| 4,867,972 A | | 9/1989 | Girardeau et al. ........... 424/81 |
| 5,317,834 A | | 6/1994 | Anderson ................ 47/48.5 |
| 5,512,534 A | | 4/1996 | Frisch et al. ............. 504/103 |
| 5,563,111 A | | 10/1996 | Hioki et al. ............. 504/116 |
| 5,723,141 A | * | 3/1998 | Kimura et al. ........ 424/421 X |
| 5,739,081 A | * | 4/1998 | Lloyd et al. ........... 504/367 X |
| 5,945,114 A | * | 8/1999 | Ogawa et al. ............ 424/408 |
| 5,965,149 A | * | 10/1999 | Silver ................ 424/408 X |

FOREIGN PATENT DOCUMENTS

| | | |
|---|---|---|
| DE | 3542440 | 6/1987 |
| EP | 0 689 866 A1 | 6/1995 |
| JP | 59186903 A | 10/1984 |
| JP | 05017305 A | 1/1993 |
| JP | 06219903 A | 1/1993 |
| JP | 06128102 A | 5/1994 |

OTHER PUBLICATIONS

Tristyrlphenol Surfactants in Agricultural Formulations Properties and Challenges in Applications, Gubelmann–Bonneau, I., ASTM Spec. Tech Publ. (1995).

* cited by examiner

*Primary Examiner*—Richard D. Lovering
(74) *Attorney, Agent, or Firm*—John A. Shedden

(57) ABSTRACT

This invention relates to certain natural diatomaceous earth granule compositions which can be broadcast, i.e., dry spread on the soil to deliver a pesticide or fertilizer. The granules retain their physical integrity when spread, and have the unique property to spontaneously disintegrate when irrigation water is applied or rainfall hits the particle. Upon wetting, the particle disintegrates (blooms) to cover the soil surface. This bloom can cover an area many times the original area covered by the granule. The granules have high loadings of the diatomaceous earth, i.e. from about 35 to about 95 weight percent and contain from about 5 to about 40 weight percent of a surfactant system which exhibits excellent disintegration; rewetting and binding properties. Bioactive compounds can be loaded at up to 60 weight percent of the granule. Bioactive compounds may be formulated products or technical grades and may be homogeneously distributed throughout the granule or spray impregnated onto the granule.

8 Claims, No Drawings

BROADCAST CARRIERS FOR PESTICIDES AND THEIR USE

This is a continuation-in-part of U.S. Ser. No. 08/715,726 filed Sep. 25, 1996 which is now abandoned.

BACKGROUND OF THE INVENTION

1. Field of the Invention

This invention relates to dry spreadable compositions; their use as carriers of bioactive materials; and methods for preparing and using said compositions. More specifically, the invention relates to surfactant-diatomaceous earth compositions for agricultural use in the form of dry spreadable granules and methods of preparing same, and even more specifically for their use in the broadcast delivery of pesticides to the soil.

2. Description of Prior Art and Problems

An organic pesticide is a bioactive material which destroys or inhibits the action of plant or animal pests. The general term pesticide includes insecticides, herbicides, fungicides, plant growth regulators, rodenticides, and miticides.

Organic pesticides are widely used in soil and turf by both consumers and commercial operators. Pesticide compounds may be used alone; however, usually they are formulated into conventional forms such as dust, granule, microgranule, wettable powder, flowable powder, emulsion, microcapsule, oil, aerosol, etc., using techniques well known in the art. To improve or stabilize the effects of the pesticide, the pesticide is blended with suitable adjuvants and then used as such or after dilution if necessary. Examples of adjuvants include carriers, diluents, spreaders, emulsifying agents, wetting agents, dispersion agents, or fixing agents.

The present invention is directed towards dry spreadable diatomaceous earth granules, and towards methods of preparing such granules, which can be applied with a dry spreader to a target area and, when exposed to water via, for example, rain or irrigation, will not only readily disintegrate, but actively spread on solid substrates so as to achieve disintegration area diameter to original granule diameter ratios larger than that heretofore realized. These dry spreadable granules are primarily used as carriers for bioactive materials such as pesticides and are easy to formulate, ship, store, and apply.

SUMMARY OF THE INVENTION

This invention provides dry spreadable compositions; their use as carriers of bioactive materials; and methods for preparing and using said compositions. Specifically, the invention relates to surfactant-diatomaceous earth compositions in the form of dry spreadable granules and methods of preparing same, and more specifically to their use in the broadcast delivery of pesticides to the soil.

The granules utilize, in addition to the diatomaceous earth, a surfactant composition designed to provide binding, rewetting and disintegration properties to the granules.

DETAILED DESCRIPTION OF THE INVENTION

The instant invention relates to the discovery of a granule which can function as a carrier for pesticides or fertilizers in a broadcast or dry spreading application. Granules for such a use have to possess certain specific characteristics which are not necessary or critical in compositions designed for admixing in large volumes of water such as tank mixes and ultimately sprayed upon sites to be treated. Bioactive-carrier compositions are often referred to as wettable powders, water dispersible granules, etc. as opposed to the dry spreadable or broadcast granules of the instant invention. Characteristics which are specific to dry spreadable granules include hardness and an ability to maintain integrity upon normal, commercial handling in a dry spreading operation and yet be capable of quickly disintegrating or scattering upon what may be a minimal exposure to water, such as, for example, a light rain.

This ability to disintegrate or scatter on a solid substrate can be primarily measured by the "Disintegration" test, as described herein, which measures what happens to a typical granule when a drop of water lands on it. Essentially, the disintegration is observed and recorded by measuring the area covered by the granule composition after being exposed to a drop or drops of water compared to the area covered by the original dry granule. Of course, the higher the ratio, the more efficacious the delivery of the bioactive that is being carried by the granule.

Once the granule has been disintegrated or scattered by the droplet, the characteristics common with the water dispersible products also come into play such as the composition's ability to disperse in large volumes of water and this property can be measured via tests such as the "Breakup" test as also described herein.

The instant invention relates to the discovery of a dry spreadable diatomaceous earth granule which, when exposed to water on a solid substrate, has a high disintegration area diameter to original granule diameter ratio. As a result, when the granules of this invention are broadcast upon the locus to be treated, e. g., soil, and then water treated, the area affected by the granule formulation is much enhanced over that realizable when the dry spreadable granules of the prior art are similarly broadcast.

By diatomaceous earth is meant a silica material characterized by a large surface area per unit volume. This is the result of an enormous number of fine pores within the structure. Diatomaceous earth is a naturally occurring material and consists mainly of accumulated shells or frustules of intricately structured amorphous hydrous silica secreted by diatoms. Diatoms are single-celled golden brown algae of the Bacillariophyceae class. The enhanced absorption/adsorption properties of the diatomaceous earth result from the very large internal surface area.

The effective diatomaceous earth of this invention has a surface area in the range of from greater than about 5 square meters per gram to less than about 90 square meters per gram, preferably from greater than about 10 to less than about 60 square meters per gram and a pore volume in the range of from greater than about 2 cubic centimeters(cc)per gram, to less than about 5 cc per gram, preferably from greater than about 3 cc per gram to less than about 4 cc per gram. Natural diatomaceous earth is preferred for this invention.

Diatomaceous earth is present in the granule composition at from about 35 to about 95 weight percent, preferably from about 50 to about 95 weight percent of the total diatomaceous earth, surfactant, and pesticide granule composition.

The surfactant composition of the present invention is present at from about 5 to about 40 weight percent, preferably from about 5 to about 20 weight percent of the total diatomaceous earth/surfactant/pesticide granule composition. The surfactant composition provides three essential properties to the dry spreadable granules.

First, the surfactant composition must act as a binder for the particles in the granule so that after the processing and agglomerating water used in the initial preparation of the granule has been driven off, residual surfactant will act as a binder to form a reasonably hard, easily handleable, i.e., a non-dusty, dry spreadable granule.

Second, the surfactant composition must possess a good rewetting ability such that when the granule is applied to the site to be treated and subsequently exposed to water, the surfactant composition will enable the water to easily penetrate the interstices of the individual diatomaceous earth particles quickly, i.e., "wet" the internal surface areas of the particles. It is theorized that this rapid rewetting of the internal surfaces results in a displacement of the air initially entrapped within the particles which then provides an additional scattering mechanism for the granules of this invention.

Third, the surfactant composition must be able to aid in the breaking up and rapid spreading of the particles initially in the granule.

In summary, the surfactant composition should possess the characteristic properties of being a good binder, rewetting agent, and disintegration aid. These properties could, of course, be found to a limited extent in a single component surfactant composition, but preferably at least a two-component composition is utilized. As will be noted below, polymeric dispersants, i.e., those with repeating units or bulky dispersants often can function as acceptable binders. A three-component surfactant composition in which each surfactant is optimized for one of the aforementioned, desired properties of the composition is most preferred.

The disintegration aids of the instant invention are usually present at from about 3 to about 15 weight percent; preferably from about 6 to about 10 weight percent based on the weight of the diatomaceous earth, surfactant, and pesticide granule composition. Certain nonionics can function as disintegration aids, preferably high molecular weight materials with repeating units, i.e., the polymerics. However, the most preferred disintegration aid surfactants of this invention are the solid (at room temperature, i.e., 24° C.), high molecular weight, polymeric anionic surfactants.

The rewetting agents of the instant invention are usually present at from about 2 to about 15 weight percent, preferably from about 2 to about 3 weight percent based on the weight of the diatomaceous earth, surfactant, and pesticide granule composition. Certain nonionics can function as rewetting agents, preferably the low molecular weight materials, i.e., the non-polymerics. However, the most preferred rewetting surfactants of this invention are the lower molecular weight, non-polymeric anionic surfactants. These surfactants are selected for their ability to move more quickly in aqueous environments than those anionics used as disintegration aids.

The binders for use in the granules of this invention, are usually present from about 0 to about 10 weight percent, preferably from about 2 to about 6 weight percent based on the weight of the diatomaceous earth, surfactant, and pesticide granule composition. These binders can be traditional binders well known in the art such as the starches, the sugars, etc., but preferably the granules of this invention use residuals or the secondary characteristics of the disintegration aids and/or rewetting agents described herein as the binding agents.

The anionics useful in the surfactant compositions of this invention include the alkyl and alkyl ether sulfates. These materials have the respective formulae $ROSO_3M$ and $RO(C_2H_4O)_xSO_3M$ wherein R is an alkyl, alkenyl or alkylauryl group of about 8 to about 22 carbon atoms, x is 1 to 10, preferably 1 to 4, and M is a water-soluble cation such as ammonium, sodium, potassium, magnesium, triethanolamine (TEA), etc. The alkyl ether sulfates useful in the present invention are condensation products of ethylene oxide and monohydric alcohols having about 8 to about 22 carbon atoms. Specific examples of the above sulfates include ammonium lauryl- sulfate, magnesium lauryl sulfate, sodium 2-ethyl-hexyl sulfate, sodium actyl sulfate, sodium oleyl sulfate, sodium tridecyl sulfate, triethanolamine lauryl sulfate, ammonium linear alcohol, ether sulfate ammonium nonylphenol ether sulfate, and ammonium monoxynol-4-sulfate.

Another suitable class of anionic surfactants are the water-soluble salts of the general formula:

$$R_1-SO_3-M$$

wherein M is a water-soluble cation and $R_1$ is selected from the group consisting of:
i) a straight or branched chain, saturated aliphatic hydrocarbon radical having from 8 to 24, preferably 12 to 18 carbon atoms;
ii) a mono-, di-, or tri- $C_1$–$C_6$ alkyl substituted aryl wherein the aryl is preferably a phenyl or naphthyl group;
iii) alpha-olefins having 12 to 24 carbon atoms, preferably 14 to 16 straight chain carbon atoms, most preferably 1-dodecene, 1-tetradecene, 1-hexadecene, 1-octadecene, 1-eicosene, and 1-tetracosene; and
iv) naphthalene-formaldehyde condensation products.

Specific examples include Supragil MNS/90, a trademark of Rhodia Inc. for an alkylnaphthalenesulfonate-formaldehyde condensate and Supragil WP, a trademark of Rhodia Inc. for a non-polymeric alkylnaphthalenesulfonate.

Additional examples of anionic synthetic surfactants which come within the terms of the present invention are: i) the isethionates, i.e., the reaction products of fatty acids esterified with isethionic acid and neutralized with sodium hydroxide where, for example, the fatty acids are derived from coconut oil; and ii) the n-methyl taurates, i.e., the sodium or potassium salts of fatty acid amides of methyl tauride in which the fatty acids, for example, are derived from coconut oil. Other anionic synthetic surfactants of this variety are set forth in U.S. Pat. Nos. 2,486,921; 2,486,922; and 2,396,278, which are incorporated herein by reference.

Still other anionic synthetic surfactants include the classes designated as the sulfosuccinates and sulfosuccinamates. These are of the general formulae:

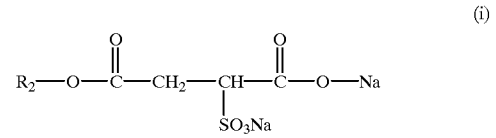

(i)

and

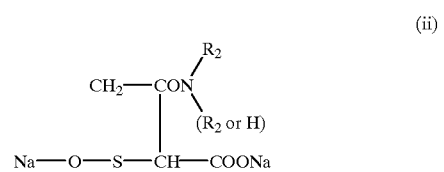

(ii)

respectively, wherein $R_2$ is a $C_2$–$C_{20}$ alkyl or alkylamido. These classes include such surface active agents as disodium N-octadecylsulfo-succinamate; tetrasodium N-(1,2-dicarboxyethyl)-N-octadecylsulfo-succinamate; diamyl ester of sodium sulfosuccinic acid; dihexyl ester of sodium sulfosuccinic acid; and dioctyl esters of sodium sulfosuccinic acid.

Another class of anionic organic surfactants are the B-alkyloxy alkane sulfonates. These compounds have the following formula:

$$R_3-\underset{\underset{H}{|}}{\overset{\overset{OR_4}{|}}{C}}-\underset{\underset{H}{|}}{\overset{\overset{H}{|}}{C}}-SO_3M$$

where $R_3$ is a straight chain alkyl group having from 6 to 20 carbon atoms, $R_4$ is a lower alkyl group having from 1 to 3 carbon atoms, and M is a water-soluble cation as hereinbefore described.

Specific examples of B-alkyloxy-alkane-1-sulfonates, or alternatively 2-alkyloxy-alkane-1-sulfonates include: potassium-B-methoxydecanesulfonate, sodium 2-methoxy-tridecanesulfonate, potassium 2-ethoxytetradecyl-sulfonate, sodium 2-isopropoxyhexadecylsulfonate, lithium 2-t-butoxytetradecylsulfonate, sodium B-methoxyoctadecylsulfonate, and ammonium B-n-propoxydodecylsulfonate.

Also to be included in the anionic class of surfactants are the disulfonates of the general formula:

$$(R_5 \text{ or } H)-\underset{SO_3M^+}{\underset{|}{\bigcirc}}-O-\underset{SO_3M^+}{\underset{|}{\bigcirc}}$$

wherein $R_5$ is a $C_8$–$C_{20}$ alkyl group and M is a water-soluble cation as hereinabove described. The preferred anionics of the disulfonate class are disodium dodecyl diphenyloxide disulfonate and ethoxylated nonylphenyl ammonium disulfonate. All of the above-described anionic surfactants and mixtures thereof may or may not be ethoxylated with from about 1 to about 10 ethylene oxide units per "R" unit.

Also useful as a disintegration aid surfactant for the granules of the instant invention are the alkali and alkali earth metal salts of the lignosulfonates.

Illustrative of the nonionics which are useful in the surfactant compositions of this invention include the following:

A) Amides such as:
  i) alkanolamides of the formula $$R-\overset{\overset{O}{\|}}{C}-N\overset{R'}{\underset{R''}{\diagup}}$$

$$-CH_2-\underset{\underset{CH_3}{|}}{CH}-OH;$$

ii) ethoxylated alkanolamides of the formula $$R-\overset{\overset{O}{\|}}{C}-N\overset{(CH_2-CH_2-O)_xH}{\underset{(CH_2-CH_2-O)_yH}{\diagup}} \quad ; \quad \text{and}$$

iii) ethylene bisamides of the formula $$R-\overset{\overset{O}{\|}}{C}-\underset{H}{\overset{|}{N}}-CH_2-CH_2-\underset{\overset{|}{C}=O}{\overset{H}{\underset{|}{N}}}-R$$

B) Esters such as:
  i) fatty acid esters of the formula $$R-\overset{\overset{O}{\|}}{C}-O-R_1;$$

ii) glycerol esters of the formula $$R-\overset{\overset{O}{\|}}{C}-O-CH_2-\underset{\underset{OH}{|}}{CH}-CH_2-O-R_1;$$

iii) ethoxylated fatty acid esters of the formula $$R-\overset{\overset{O}{\|}}{C}-O-(CH_2CH_2O)_x-R_1;$$

iv) sorbitan esters of the formula

[structure of sorbitan ester with HO, OH groups on tetrahydrofuran ring, CH—CH$_2$—O—C(=O)—R; OH]   and v) ethoxylated sorbitan esters of the formula $$H-(OCH_2CH_2)_n-O\quad\quad O-(CH_2CH_2O)_x-H$$
[ethoxylated sorbitan ester structure with CH—CH$_2$—O—C(=O)—R and O—(CH$_2$CH$_2$O)$_y$H]

C) Ethoxylates such as:
i) alkylphenol ethoxylates of the formula

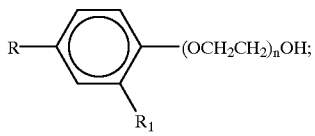

ii) alcohol ethoxylates of the formula

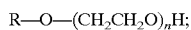

R—O—(CH$_2$CH$_2$O)$_n$H;

iii) tristyrylphenol ethoxylates of the formula

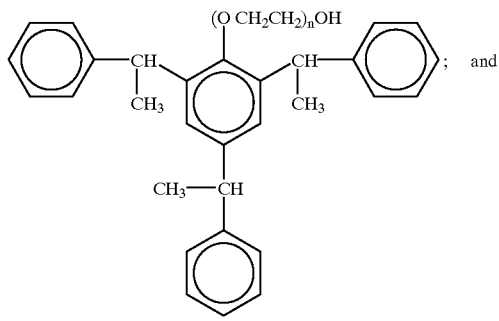

iv) mercaptan ethoxylates of the formula

R—S—(CH$_2$CH$_2$O)$_n$H

D) End-capped and EO/PO block copolymers such as:
i) alcohol alkoxylates of the formula

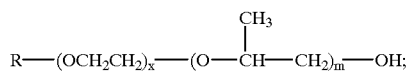

ii) ethylene oxide/propylene oxide block copolymers of the formula

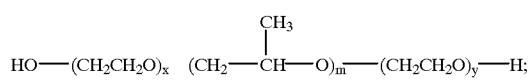

iii) copolymers of the formula

iv) chlorine capped ethoxylates of the formula

R—(OCH$_2$CH$_2$)$_x$Cl; and v) tetra-functional block copolymers of the formula

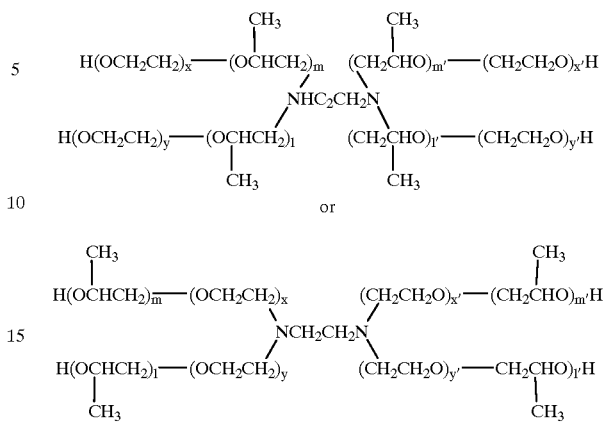

wherein
R is a fatty alkyl group, preferably a C$_6$–C$_{22}$ fatty alkyl group, most preferably a C$_8$–C$_{18}$ fatty alkyl group;

R$_1$ is —H or a fatty alkyl group, preferably —H or a C$_6$–C$_{22}$ fatty alkyl group, most preferably —H or a C$_8$–C$_{18}$ fatty alkyl group;

x, x', y, y' and n are each independently moles of ethylene oxide preferably 1 to 300; most preferably 1 to 150; and m, m', l and l' are each independently moles of propylene oxide, preferably 1 to 300; most preferably 1 to 150.

Among the preferred disintegration aids are: the water soluble salts of alkylnaphthalenesulfonate-formaldehyde condensates; sodium lignosulfonate, diphenyloxide, ethoxylated tristyrylphenols, ethoxylated tristyrylphenol phosphates, the ethylene oxide/propylene oxide block copolymers, and acid, salts and copolymers of the polyacrylates.

Among the preferred rewetting agents are: the alkylnaphthalenesulfonates, sodium methyloleoyl taurate, the sulfosuccinates, the carboxylates, the alkylarylsulfonates, the ethoxylated alkyl phenols and the ethoxylated alcohols.

Although electrostatic disintegration aids such as the anionics are preferred, steric disintegration aids such as the polyvinyl alcohols can also be used.

Although the dry spreadable granules of this invention can be prepared by a standard pan granulation process, it is preferred that the granules, with or without the presence of a pesticide, are prepared via a homogeneous extrusion process. Of note, granules that are prepared in the absence of a pesticide by the homogeneous extrusion process can subsequently be sprayed with pesticide to adhere same to the granules.

The extrusion granulation process is illustrated as follows: First, each component is weighed, combined, and blended. Water is then added with continuous mixing until from about 10 to about 50 weight percent, preferably about 25 to about 45 weight percent moisture content is realized. The mixture is then fed to a low pressure basket or radial extruder. The wet mass is extruded through a die having openings with diameters of from about 0.8 mm to about 2.0 mm, preferably about 1 mm. The extrudate is then fed to a vibratory fluidized bed dryer which reduces the moisture content to below about 5; preferably to below about 4 and most preferably below about 2.5 weight percent; the weight percents being based on the total weight of the composition at that respective step in the process.

In the spray formulation process, diatomaceous earth/surfactant granules are prepared by the homogeneous extrusion process described above, and the pesticide is dissolved in an appropriate solvent, e.g., iso-propanol or xylene in an amount sufficient to make a suitably viscous sprayable solution, typically from about 10 to above about 50 percent by weight pesticide and sprayed onto the granules. It is also recognized that certain actives can be melt sprayed onto the granules. The spray is continued onto the granules with continuous mixing. The sprayed granules are then dried, preferably in a fluid-bed dryer to final moisture content as indicated above. The product, however made, is then sieved in a particle classifier to remove oversized and undersized granules. It is preferred that the final product is that which passes through a 10 mesh screen but will not pass through a 60 mesh screen.

A serendipitous and unusual characteristic of the diatomaceous earth granules of this invention, which are designed to be broadcast or dry spreadable, is the speed with which these granules will disperse in water. When the granules of this invention with size of 1×5 (diameter x length in millimeters) are gently placed on the surface of cold tap water (about 20° C.) in, for example, a beaker, the granules, with no mechanical energy input, will completely disintegrate within two (2) to ten (10) seconds. Most conventional water dispersible granules require from five (5) to thirty (30) or more inversions of the beaker to effect a similar result in a similar time period.

As indicated above, a further preferred embodiment of the present invention is the use of the granules described above as a carrier for the broadcast delivery of pesticides, e.g., insecticides, herbicides, fungicides and plant growth regulators. For the purpose of expediency, the term "pesticide" herein is also defined to include fertilizers such as urea. Specifically, the present invention is directed towards a granule as described above, methods of preparing said granules, use of said granules as a carrier to broadcast pesticides, and the pesticidal granule per se.

Although the instant invention is universally applicable to all pesticides, the preferred classes of pesticides include the pyridines, carbamates and dithiocarbamates, chlorinated hydrocarbons, organophosphorous compounds, dinitroanilines, diphenyl ethers and synthetic pyrethroid compounds.

Other well known specific pesticides include oxidiazon, iprodione, aluminum salt of ethyl hydrogen phosphonate, (fosetyl Al), and those described in U.S. Pat. No. 5,317,834 which is incorporated herein by reference.

In this embodiment, the pesticide is present in the granule described above, in an effective amount that will not interfere with the desired properties of the granules, i.e., the dry spreadability. For example, the pesticide must not be present in an amount that would result in "sticky" granules which cannot be dry spread.

Commercial water-dispersible pesticide granules (WDGs) usually contain relatively high loadings of the pesticidal active because they are designed to be added to, and therefore significantly diluted with water and the resulting aqueous solution/suspension sprayed upon the locus to be treated. The granules of the instant invention, on the other hand, are designed to be dry spread directly on the locus to be treated and thus usually contain relatively lower levels of pesticidal active than the WDGs.

Although, in the present invention, the pesticide may be present up to about 60 weight percent, the pesticide is preferably present at from about 0.005–30 weight percent, most preferably 0.5–20 weight percent, based upon the total weight of the diatomaceous earth, surfactant, and pesticide in the granule.

The granules, containing the pesticide can be broadcast, that is, applied with a dry spreader to a target area and, when exposed to water via, for example, rain or irrigation, readily decompose or disintegrate and actively spread. The highly active disintegration process allows the pesticide to be delivered over a larger surface area than that immediately covered by the original granules resulting in a much more effective delivery of the pesticides to the targeted area.

The following examples are intended to illustrate the claimed invention and are not in any way designed to limit its scope. Numerous additional embodiments within the scope and spirit of the claimed invention will become apparent to those skilled in the art.

Materials

The following materials are used in the Examples. Each of the carrier compounds was obtained from Celite Corp., Lompac, Calif.

| Diatomaceous Earth Compound | How Manufactured |
| --- | --- |
| Celite 209 | Natural diatomaceous earth |
| Celite 392 | Natural diatomaceous earth |
| Celite 500 | Natural diatomaceous earth |
| Celite 503 | Flux Calcinated diatomaceous earth |
| Celite 560 | Flux Calcinated diatomaceous earth |

| Synthetic Compound | How Manufactured |
| --- | --- |
| Microcel E | Calcium silicate |
| Microcel T-49 | Calcium silicate |
| Microcel A | Calcium silicate |
| Microcel B | Calcium silicate |
| Celite R-685 | Magnesium silicate |

Surfactants:

Supragil WP: a trademark of Rhodia Inc. for an alkylnaphthalenesulfonate.

Supragil MNS/90: a trademark of Rhodia Inc. for an alkylnaphthalenesulfonate-formaldehyde condensate.

Soprophor S/40-P: a trademark of Rhodia Inc. for a tristyrylphenol ethoxylate.

Tests

The Disintegration Test: the Disintegration test is a determination at room temperature of the degree of breakup of the granules in a petri dish after contact with droplets of water.

To determine the Disintegration, a test is conducted as follows:

Approximately 0.1–0.2 grams of granules are placed into a petri dish. The granules are placed approximately 5 mm apart. A single droplet of water is squirted onto each granule. After a number of seconds, the granule is observed and rated as discussed below. Application of single drops of water is continued until total disintegration occurs.

Disintegration is measured on a scale of 0 to 9, with 9 being the highest and 0 being the lowest. A rating of 9 indicates that the granule disintegrates immediately on contact with water, spreading out evenly without additional water needed. A rating of 8 indicates that the granule loses integrity immediately on contact with water and some material spreads out from the original granule. On contact with a second water droplet, the material spreads easily. A rating of 7 indicates that the granule loses integrity immediately on contact with water however almost no material spreads out from the original body of the droplet. On contact with a second water droplet, the material disperses easily. A rating of 6 means that the granule loses integrity after about 3 seconds of contact with the first droplet; almost no material spreads out from the original body of the granule; and on contact with the second droplet, the material disperses easily. A rating of 5 indicates that the granule loses integrity after about 3 seconds from contact with water. On contact with the second droplet, the material disperses into very small fragments. The fragments disperses totally on contact with a third droplet. A rating of 4 indicates that the granule loses integrity after about 5 seconds from contact with the first droplet. On contact with the second droplet, the material disperses into fragments approximately one-quarter of the size of the original granule. The fragments disperse totally with one or two more droplets. A rating of 3 indicates that the granule loses integrity after about 10 seconds from contact with the first droplet. On contact with the second droplet, the material disperses into fragments approximately one-quarter to one-half the size of the original granule. The fragments disperse on contact with 3 or 4 more droplets. With a rating of 2 the granule loses integrity after contact with several droplets after 10 to 15 seconds. It requires several more droplets to break into fragments one-half the size of the original granule. Several more droplets are required for total dispersion. A rating of 1 indicates that the granule does not lose integrity until after soaking in water for over one minute. The pieces produced require substantial additional droplets to disperse into fragments. A rating of 0 indicates that water has no effect on the granule.

Breakup Test: To determine Breakup, a graduated cylinder test is conducted as follows:

Approximately 0.2 grams of granule formulation are placed into a graduated cylinder containing 100 mls. of water at room temperature. The results are evaluated on a scale of 0 to 9 with 9 being the highest. A rating of 9 indicates that the granules immediately disperse into a cloud of material which very slowly spreads downward, eventually filling the entire column. A rating of 8 indicates that the majority of the granules immediately disperse into a cloud of material with the remaining material slowly migrating downward in the form of very small fragments. The fragments totally disperse before reaching the one-half way (50 ml) mark of the column. The entire column eventually fills with material. No fragments reach the bottom of the column. A rating of 7 indicates that the majority of the granules immediately disperse into a cloud of material, with the remaining material migrating downward in the form of small fragments which totally disperse before reaching the three-quarter (25 ml) mark of the column. The entire column eventually fills with material. No fragments reach the bottom of the column. A rating of 6 indicates that approximately one-half of the granules immediately disperse into a cloud of material. The remaining granules migrate downward in the form of fragments. The majority of fragments totally disperse before reaching the bottom. A small amount of fragments reach the bottom of the cylinder. A rating of 5 indicates that small amounts of the granules disperse into a cloud of material. The remaining material migrates downward in the form of fragments, with approximately ¼ of the original mass of granules reaching the bottom of the cylinder as fragments. A rating of 4 indicates that no cloud of material forms. The granules break into fragments and disperse as they migrate downward. Approximately one-half of the original mass of granules reaches the bottom of the cylinder as fragments. A rating of 3 indicates that no cloud of material forms. The granules break into fragments and disperse as they migrate downward. Approximately three-quarters of the original mass of granules reaches the bottom of the cylinder as fragments. A rating of 2 indicates that a small amount of granules break into fragments. The majority of the granules sink to the bottom of the cylinder without breaking apart. A rating of 1 means that no granules break into fragments. The granules sink rapidly to the bottom of the cylinder with a very small amount of material separating from the granules. About 95–99% of the material reaches the bottom of the cylinder in granule form. A rating of 0 indicates that the granules sink to the bottom of the cylinder unaffected by the water.

Overall Rating: An overall rating is given each granule formulation based on the Disintegration and Breakup results as follows: if both are individually 6 or better, i.e., from 6 to 9, the formulation is given a "Good" rating; if both are individually 4 or better, i.e., within the range of 4 to 9, the formulation is given a "Fair" rating; and if below the "Fair" standard, the formulation is given a "Poor" rating.

EXAMPLE 1

Two different diatomaceous earth surfactant granule formulations are prepared as follows: 85 grams of the diatomaceous earth; 8 grams of Supragil MNS/90; 4 grams of Soprophor S/40-P; and 3 grams of Supragil WP are weighed on a balance; added to a food processor; and mixed for 2 minutes at the highest rate. Then about 90 grams of water is added and the material mixed for an additional 2 minutes. Care is taken to ensure good uniformity of the material. The mass is then transferred to a benchtop basket extruder and extruded through die holes as indicated below. The wet granules are dried in a fluid-bed dryer at a temperature of 50–60° C. for about 10 minutes. The moisture content of the granules after drying is from about 2.2 to 2.5 weight percent.

Disintegration and Breakup tests are conducted on two granule sizes made from Celite 500 and one granule size made from Celite 209. The results are as indicated in Table I below.

TABLE I

| Sample | Granule Size | Disintegration | Breakup | Rating |
| --- | --- | --- | --- | --- |
| Celite 500 | 1 mm | 8 | 8 | Good |
| Celite 500 | 2 mm | 7 | 6 | Good |
| Celite 209 | 1 mm | 8 | 8 | Good |

EXAMPLE 2

A series of dry spreadable granules is prepared as described above using several different diatomaceous earth samples. The granules are then dried in two sets; one at 50° C. for 20 minutes and the other at 100° C. for 10 minutes. The final moisture content for all granules is less than 4%.

For comparison, granules containing synthetic calcium and magnesium silicates are also prepared.

The formulation for all granules is as follows:

|  | Weight Percent (%) (Based on Total Weight) |
|---|---|
| Diatomaceous earth or synthetic silicate compound | 85 |
| Supragil WP | 3 |
| Supragil MNS/90 | 8 |
| Soprophor S/40P | 4 |

The performance results are as indicated in Table II below.

TABLE II

| | Breakup | |
|---|---|---|
| Sample | 50° C. | 100° C. |
| Celite 209 | 8 | 8 |
| Celite 392 | 7 | 7 |
| Celite 500 | 8 | 8 |
| Celite 503 | 2 | 2 |
| Celite 560 | 2 | 3 |
| Microcel E | 0 | 0 |
| Microcel T-49 | 0 | 0 |
| Microcel A | 0 | 0 |
| Microcel B | 0 | 0 |
| Celite R-685 | 2 | 2 |

The results of the Disintegration tests are as shown below in Table III.

Table III

| Sample | Disintegration 50° C. | Disintegration 100° C. |
|---|---|---|
| Celite 209 | 8 | 8 |
| Celite 392 | 7 | 7 |
| Celite 500 | 8 | 8 |
| Celite 503 | 2 | 2 |
| Celite 560 | 2 | 3 |
| Microcel E | 0 | 0 |
| Microcel T-49 | 0 | 0 |
| Microcel A | 0 | 0 |
| Microcel B | 0 | 0 |
| Celite R-685 | 2 | 2 |

The petri dish disintegration performance of the natural diatomaceous earth samples of this invention are much superior to that of the flux calcinated natural diatomaceous earths and the synthetically-made materials.

EXAMPLE 4

The physical properties of the dry spreadable granules of Examples 2 and 3 are determined and set forth in Table IV below.

TABLE IV

| | Diatomaceous Earth | | | | | | Granule | |
|---|---|---|---|---|---|---|---|---|
| Sample | WA[1] | MpaS[2] | SA[3] | MPos[4] | PV[5] | D[6] | Disintegration | Break up |
| Celite 209 | 185 | 5 | 10–20 | 0.88 | 3 | 8 | 8 | 8 |
| Celite 392 | 215 | 25 | 10–20 | 2.6 | 3.2 | 8 | 7 | 7 |
| Celite 500 | 230 | 22 | 19 | 2.5 | 3.4 | 7 | 8 | 8 |
| Celite 503 | 220 | 31 | 1.0 | 9.5 | 2.6 | 12 | 2 | 2 |
| Ceiite 560 | 240 | 52 | 0.7 | 26.6 | 2.6 | 16 | 2 | 2 |
| Celite R685 | * | 10 | 175 | 2 | 5.5 | 17 | 2 | 2 |
| Microcel A | 430 | 17 | 100 | 1.6 | 5.2 | 7.2 | 0 | 0 |
| Microcel B | 300 | 14 | 91 | 2.6 | 3.8 | 14.6 | 0 | 0 |
| Microcel E | 500 | 23 | 120 | 1.8 | 5.5 | 5.8 | 0 | 0 |
| Microcel T-49 | 315 | 7 | 105 | 2.2 | 3.7 | 11.6 | 0 | 0 |

[1]Water Absorption, % by Weight
[2]Median Particle Size - microns
[3]Surface Area - (meters$^2$/gram)
[4]Median Pore Size - microns
[5]Pore Volume - cc/g
[6]Bulk Density - lb/cubic foot
*hydrophobic From the results shown in Table II above, the performance of the natural diatomaceous earth samples with internal surface areas and pore volumes within the ranges of this invention, is superior to that of the flux calcinated natural diatomaceous earth and synthetically made materials. The natural diatomaceous earth samples show overall better Breakup in water.

For Celite 209, 392, and 500, Breakup values are 7–8. From Table II, one also observes that drying temperature has little effect on Breakup.

EXAMPLE 3

The series of dry spreadable carrier granules of Example 2 are tested to determine the Disintegration of the granules.

Thus, as can be seen by the results in Table IV above, unexpectedly superior Breakup and Disintegration performance results can be realized with the granules of this invention when natural diatomaceous earth having a surface area in the range of from greater than about 5 to less than about 90 square meters per gram; preferably, from greater than about 10 to less than about 60 meters per. gram and a pore volume in the range of from greater than about 2 cubic centimeters (cc) per gram to less than about 5 cc per gram, preferably, from greater than about 3 cc per gram to less than about 4 cc per gram, is utilized.

EXAMPLE 5

The following is illustrative of the preparation of a homogeneous dry spreadable granule containing 2 weight percent (active ingredient (a.i.)) chlorpyrifos.

The homogeneous formulation is composed of:

2.0 wt. % Chlorpyrifos 3.0 wt. % Supragil WP 4.0 wt. % Soprophor S/40-P 8.0 wt. % Supragil MNS/90

83.0 wt. % Diatomaceous Earth (Celite 500)

The test material is prepared by using a benchtop basket extruder. The batch size is 50 grams. First, chlorpyrifos technical (99%, low odor), is dissolved in iso-propanol to make a 20 weight percent chlorpyrifos stock solution. To make a batch of 2 weight percent a.i. homogeneous formulation, the following materials are weighed on a balance and mixed for 2 minutes at the highest rate in a compact food processor: 41.5 grams Celite 500, 4.0 grams Supragil MNS/90, 2.0 grams Soprophor S/40-P, and 1.5 grams Supragil WP. Then, 5 grams of the 20 weight percent chlorpyrifos (in iso-propanol) solution is added using a pipet. The mixture is mixed for one more minute. Then 44.5–45.5 grams of water is added and the material mixed for another 2 minutes. Care is taken to ensure a good uniformity of the material. The mass is transferred to a benchtop basket extruder and extruded. The dye has 1 mm holes. The wet granules are dried in a fluid-bed dryer at a temperature of 50° C. (set-point) for 10 minutes. The actual drying temperature is about 60° C. The moisture content of the granules after the dryer is 2.2–2.5 weight percent. The dry granules have a good visual flowability. The tap density of the granules is 0.35 grams/cc. The Disintegration rating from the petri dish test is 8. From the graduated cylinder test, the Breakup rating is 7–8.

The moisture content of raw material Celite 500 is 3.7 weight percent. So, the weight of raw material Celite 500 is close to the dry weight of Celite 500. According to the product specifications of Supragil MNS/90, Soprophor S/40-P, and Supragil WP, the moisture contents of these components are no higher than 2 weight percent. Also, samples of chlorpyrifos technical were tested for volatile materials in a ventilating oven. The weight loss after 2 hours at 141° F. (=60.5° C.) was only 0.6 weight percent. Hence, the granules should not lose significant amount of chlorpyrifos at the dryer. Therefore, the dry spreadable granular product as manufactured above contains approximately 2.0 weight percent chlorpyrifos.

EXAMPLE 6

The following is illustrative of the preparation of a 2 weight percent a.i. chlorpyrifos dry spreadable granule whereby the chlorpyrifos is sprayed onto the diatomaceous earth-surfactant substrate to make the pesticidal-carrier granules.

The activity and final formulation of the 2 weight percent a.i. chlorpyrifos spray-on granule is almost identical to that of the 2 weight percent a.i. chlorpyrifos homogeneous granule. However, the spray-on granule is prepared using a different process from that of the homogeneous formulation. An inert dry spreadable granule is prepared first, then chlorpyrifos solution (in iso-propanol) is sprayed on the inert granules to make 2 weight percent a.i. chlorpyrifos spray-on material. The inert granule formulation is composed of the following ingredients:

3.0 weight percent Supragil WP 4.0 weight percent Soprophor S/40-P 8.0 weight percent Supragil MNS/90

85.0 weight percent Diatomaceous Earth (Celite 500)

The inert material is made in a process similar to that used to prepare the 2 weight percent a.i. chlorpyrifos homogeneous granule. To make a 50 gram batch, the following ingredients are mixed in a food processor: 42.5 grams Celite 500, 4.0 grams Supragil MNS/90, 2.0 grams Soprophor S/40-P, and 1.5 grams Supragil WP. Then, 46.5–47.0 grams of water is added and the material is well-mixed to become an extrudable mass. The mass is transferred to the benchtop basket extruder and extruded. The benchtop extruder has a 1 mm dye. The wet granules are dried in the fluid-bed dryer at the temperature of 50° C. (set-point) for 8 minutes. The moisture content of the inert granules after drying is 2.1–4.6 weight percent. The dry inert granules have a good visual flowability. The tap density of the inert granules is 0.34 grams/cc. The Disintegration rating from the petri dish test and the Breakup rating from the graduated cylinder test are 8 and 8 respectively.

The next step is to spray the pesticide active ingredient onto the inert material. Chlorpyrifos (99%, low odor), is dissolved in iso-propanol to make a 20 weight percent solution. A benchtop tumbling mixer is used. 98 grams of the above inert granules are added to the mixer and the mixer turned on. Then 10.0 grams of 20% chlorpyrifos (in iso-propanol) solution are sprayed onto the inert granules using a hand sprayer in a time period of 30 seconds. The material is mixed for another 5 minutes. The spray-on granules are dried in the fluid bed dryer at a temperature of 50° C. (set-point) for 8 minutes. The moisture content of the granules after the dryer is 2.1–2.2 weight percent. The dry granules have a good visual flowability. The tap density of the granules is 0.35 grams/cc. The Disintegration rating from the petri dish test and the Breakup rating from the graduated cylinder test are 8 and 8 respectively.

EXAMPLE 7

Additional dry spreadable granules are made by the pesticidal spray-on process described in Example VI using different final concentrations of chlorpyrifos on the granules. The performance results are as indicated in Table V below.

TABLE V

| Sample | Disintegration | Breakup |
| --- | --- | --- |
| 1.4% a.i. Chlorpyrifos | 8 | — |
| 2.0% a.i. Chlorpyrifos | 8 | 8 |
| 2.1% a.i. Chlorpyrifos | 8 | — |

EXAMPLE 8

A series of dry spreadable granules is prepared as described above using Celite 500 and several different pesticides.

The following pesticides are used:

Oxadiazon: Chipco® Ronstar® 50WP Brand Herbicide, a trademark of Rhone-Poulenc for a formulated wettable powder containing 50% oxadiazon, a herbicide.

Fosetyl Al: Chipco® Aliette® WDG Fungicide, a trademark of Rhone-Poulenc for a water dispersible granule containing 80% aluminum salt of ethyl hydrogen phosphonate, (fosetyl-Al), a fungicide.

Iprodione: Chipco® 26109, a trademark of Rhone-Poulenc for a formulated wettable powder containing 50% iprodione, a fungicide.

Chlorpyrifos: Chlorpyrifos Technical (99% a.i.) obtained from Micro Flo Company, an insecticide.

Mancozeb (DG): a coordination product of $Zn^{2+}$ and manganese ethylene bis(dithiocarbamate), (75% a.i.) a fungicide, obtained from Lesco Inc.

Mancozeb (Dithane): a coordination product of $Zn^{2+}$ and manganese ethylene bis(dithiocarbamate) (80–85% a.i.), a fungicide, obtained from Rohm & Haas Company.

Chlorothalonil: Bravo® W-75, a trademark of ISK Biotech (75% a.i.) and ii) 5% Daconil, a trademark of the Anderson's Lawn Product Company (5% a.i.), terachloroisophthalonitril, a fungicide.

Prodiamine: Barricade 65 WG Brand herbicide, a trademark of Sandoz Crop Protection Corp. for a formulated water dispersible granule containing Prodiamine (65% a.i.).

The formulation for all granules which are prepared by the aforedescribed homogeneous process (except where indicated) and except those containing chlorpyrifos, is as follows:

|  | Weight Percent (%) (Based on Total Weight) |
|---|---|
| Celite 500 and pesticide (Total of Two) | 85 |
| Supragil WP | 3 |
| Supragil MNS 90 | 8 |
| Soprohor S/40P | 4 |

Although the amount of the pesticide may be varied, see Tables VI and VII, "% Active", the total amount of pesticide and Celite 500 remains constant at 85% of the total weight.

The granules containing chlorpyrifos are prepared as described in Example 5.

Table VI represents performance results realized using formulated pesticidal products as the pesticidal starting material in the granules of this invention whereas Table VII represents performance results realized using "technical" grade pesticides as the pesticidal starting material.

Breakup and Disintegration values for each of the formulations utilized are determined and are listed below in Tables VI and VII. In addition, a determination of the overall rating of each sample is shown in the last column.

The first series of granules in Table VI are formulated using Ronstar 50WP, a wettable powder containing 50% oxadiazon as the active herbicide ingredient. The granules in this series contain 0.5, 1.0, 2, 5, 10, 15, 20 and 30 weight percent oxadiazon based on the total weight of a granule of 1.0 mm size.

As can be seen in Table VI, good results are obtained for up to 15 weight percent oxadiazon; above 15 weight percent disintegration is reduced. Therefore it appears that 15% is the preferred upper limit of the range defining peak performance.

The next series of granules in Table VI are formulated using Aliette, a fungicide containing ethyl hydrogen phosphonate (fosetyl Al) as the active pesticide ingredient. This series contains 0.8, 1.6, 4, 8, and 16 weight percent active ingredient based on the total weight of a granule of 1.0 mm size. The results shown in Table VI indicate that with up to 4 weight percent Aliette, good results are obtained.

The third series of granules in Table VI are formulated using Chipco 26019, a fungicide containing 50% iprodione as the active ingredient. This series contains 0.5, 1.0, 2.5, 5, 10, 15, 20 and 30 weight percent active ingredient based upon the total weight of a granule of size 1.0 mm. As can be seen in Table VI, good results are obtained for up to 15 weight percent pesticide; it appears that 15% is the preferred upper limit for peak performance with respect to disintegration.

A fourth set of samples, containing chlorpyrifos, an insecticide, is prepared as described above. This series contains 2.0, 5.0, 10.0 and 15.0 weight percent active ingredient based upon the total weight of a granule of 1.0 mm size. As can be seen in Table VI, granules containing 2.0%, 5.0%, and 10.0% chlorpyrifos perform well.

Test results from various other pesticides are as indicated in Table VI. The overall results from these different active ingredients indicate that formulated pesticides can be loaded onto the dry spreadable granules of this invention to a certain degree. The approximate peak values at maximum loading when using the formulated pesticides in the studies are:

| Oxadiazon | 15% |
|---|---|
| Ethyl Hydrogen Phosphonate | 4% |
| Iprodione | 15% |
| Chlorpyrifos | 10% |
| Mancozeb (DG) | 10% |
| Mancozeb (Dithane) | 15% |
| Chlorothalanil | >5% |

(Above percents are weight percents based upon the total granule weight.) Beyond the peak values there is reduced disintegration indicating that at a point, the presence of the formulated pesticide interferes with the ability of the granule to disintegrate rapidly in water. However, in the instant invention, these peak values are equal to or superior to concentrations found in existing granular spreadable products as will be seen in Table VIII below.

TABLE VI

| Carrier | Pesticide | % Active | Disintegration | Breakup | Rating |
|---|---|---|---|---|---|
| Celite 500 | Oxadiazon | 0.5 | 8 | 8 | Good |
| Celite 500 | Oxadiazon | 1 | 8 | 8 | Good |
| Celite 500 | Oxadiazon | 2 | 8 | 8 | Good |
| Celite 500 | Oxadiazon | 5 | 8 | 8 | Good |
| Celite 500 | Oxadiazon | 10 | 8 | 8 | Good |
| Celite 500 | Oxadiazon | 15 | 7 | 8 | Good |
| Celite 500 | Oxadiazon | 20 | 5 | 5 | Fair |
| Celite 500 | Oxadiazon | 30 | 2 | 2 | Poor |
| Celite 500 | fosetyl Al | 0.8 | 8 | 8 | Good |
| Celite 500 | fosetyl Al | 1.6 | 8 | 7 | Good |
| Celite 500 | fosetyl Al | 4 | 7 | 6 | Good |
| Celite 500 | fosetyl Al | 8 | 6 | 3 | Fair |
| Celite 500 | fosetyl Al | 16 | 2 | 0 | Poor |
| Celite 500 | Iprodione | 0.5 | 8 | 8 | Good |
| Celite 500 | Iprodione | 1 | 8 | 8 | Good |
| Celite 500 | Iprodione | 2.5 | 8 | 8 | Good |
| Celite 500 | Iprodione | 5 | 8 | 8 | Good |
| Celite 500 | Iprodione | 10 | 8 | 8 | Good |
| Celite 500 | Iprodione | 15 | 7 | 7 | Good |
| Celite 500 | Iprodione | 20 | 3 | 2 | Poor |
| Celite 500 | Iprodione | 30 | 1 | 0 | Poor |
| Celite 500 | Chlorpyrifos | 2 | 8 | 8 | Good |
| Celite 500 | Chlorpyrifos | 5 | 7 | 7 | Good |
| Celite 500 | Chlorpyrifos | 10 | 7 | 6 | Good |
| Celite 500 | Chlorpyrifos | 15 | 6 | 5 | Fair |
| Celite 500 | Chlorpyrifos Spray* | 1.4 | 8 | — | Good |
| Celite 500 | Chlorpyrifos Spray* | 2.1 | 8 | — | Good |
| Celite 500 | Mancozeb (DG) | 1 | 8 | 7 | Good |
| Celite 500 | Mancozeb (DG) | 2 | 8 | 7 | Good |
| Celite 500 | Mancozeb (DG) | 5 | 7 | 6 | Good |

TABLE VI-continued

| Carrier | Pesticide | % Active | Disintegration | Breakup | Rating |
|---|---|---|---|---|---|
| Celite 500 | Mancozeb (DG) | 10 | 7 | 6 | Good |
| Celite 500 | Mancozeb (DG) | 20 | 6 | 5 | Fair |
| Celite 500 | Mancozeb (DG) | 30 | 5 | 3 | Fair |
| Celite 500 | Mancozeb (Dithane) | 15 | 7 | 6 | Good |
| Celite 500 | Mancozeb (Dithane) | 30 | 6 | 5 | Fair |
| Celite 500 | Chlorothalanil | 2 | 8 | 8 | Good |
| Celite 500 | Chlorothalanil | 5 | 7 | 8 | Good |
| Celite 500 | Prodiamine | 6.5 | 8 | 7 | Good |
| Celite 501 | Prodiamine | 13 | 6 | 6 | Good |
| Celite 502 | Prodiamine | 19.5 | 3 | 4 | Poor |

*Prepared by a spray process as follows:
1.) Inert granule is prepared as in Example 1.
2.) Micro Flo Chlorpyrifos Pro 6mup (obtained from Micro Flo Company) is diluted in xylene at a weight ratio of 1 to 9.
3.) 5 grams of inert granule is placed in a petri dish with a diameter of 10 cm. The granules are spread out as a thin layer.
4.) The chlorpyrifos/xylene solution is sprayed on the granules using a hand sprayer.
5.) The wet granules are dried in a fluid-bed dryer at a temperature of 80° C. for 20 minutes.

TABLE VII

As previously indicated, the following Table VII presents performance results realized using technical grade pesticides as the pesticidal starting material in the granule homogeneous formulation process of this invention.

| Carrier | Pesticide | % Active | Disintegration | Breakup | Rating |
|---|---|---|---|---|---|
| Celite 500 | Oxadiazon, Tech | 20 | 6 | 7 | Good |
| Celite 500 | Oxadiazon, Tech | 30 | 7 | 7 | Good |
| Celite 500 | Oxadiazon, Tech | 40 | 6 | 7 | Good |
| Celite 500 | Oxadiazon, Tech | 50 | 5 | 5 | Fair |
| Celite 500 | Iprodione, Tech | 20 | 7 | 7 | Good |
| Celite 500 | Iprodione, Tech | 30 | 7 | 7 | Good |
| Celite 500 | Iprodione, Tech | 40 | 4 | 5 | Fair |

The above Table VII illustrates the significantly higher pesticidal loadings that can be realized by using technical grade pesticide as the starting material in the dry spreadable granules of this invention as compared to the already superior loadings achievable with formulated pesticide usage that was shown in Table VI. It is believed that the "technical" provides better performance than use of the formulated starting material because of the absence of carrier and formulation aids that are contained in the formulated products, i. e., incorrect surfactant combinations can actually interfere with the desirable dry spreadable performance characteristics.

For comparative purposes, and to vividly underscore the unexpectedly high pesticidal loadings realizable with the granules of this invention, the following Table VIII contains a listing of typical, commercially available dry spreadable, granular pesticidal products and their respective pesticidal (% active) loadings.

TABLE VIII

| Product | % a.i. | Generic Name | Manufacturer |
|---|---|---|---|
| Dursban | 2.32 | Chlorpyrifos | The Andersons Lawn Products Division Maumee, OH |
| Insecticide III | 1.34 | Chlorpyrifos | The O. M. Scott and Sons Company Marysville, OH |
| Ronstar G | 2 | Oxadiazon | Rhone Poulenc Ag Company Research Triangle Park, NC |
| Goosegrass/ Crabgrass Control | 1.31 5.25 | Oxadiazon Bensulide | The O. M. Scott and Sons Company Marysville, OH |
| 5% Daconil Fungicide | 5 | Chlorothalonil | The Andersons Lawn Products Division Maumee, OH |
| Fungicide X | 1.3 | Iprodione | The O. M. Scott and Sons Company Marysville, OH |

EXAMPLE 9

Granules of this invention are prepared by the homogeneous process as set forth in Example 5 with the chlorpyrifos being replaced by 17.5% urea fertilizer. The performance results are given in Table IX below.

TABLE IX

| Sample | % Active | Disintegration | Breakup | Rating |
|---|---|---|---|---|
| Celite 500 | Urea (17.5%) | 8 | 8 | Good |

EXAMPLE 10

For purposes of comparison, various other materials well known in the pesticidal carrier art, are substituted for the diatomaceous earth and examined in the dry spreadable granule surfactant systems of this invention. At weight loadings of 85%, the materials are substituted for the diatomaceous earth in the process as set forth in Example 1. The performance results are given in Table X below.

TABLE X

| Sample | Disintegration | Breakup | Rating |
|---|---|---|---|
| Kaolinite | 0 | 0 | Poor |
| Lattice NT | 1 | 0 | Poor |
| Attacote | 3 | 1 | Poor |
| AC FD 181 | 0 | 0 | Poor |
| Sulfur | 1 | 1 | Poor |
| Vermiculite Dust | 3 | 1 | Poor |

EXAMPLE 11

For additional comparative purposes, a synergistic blend of an anionic surfactant and a lignosulfonate (Ag RHO SP-33D, a trademark of Rhodia, Inc.) is substituted for the Supragil MNS/90 surfactant of this invention in the process of Example 5 and homogeneous process granules are prepared with three pesticides as set forth in Table XI below together with performance results.

TABLE XI

| Sample | Pesticide | % Active | Disintegration | Breakup | Rating |
|---|---|---|---|---|---|
| Celite 500 | Mancozeb (DG) | 10 | 7 | 6 | Good |

TABLE XI-continued

| Sample | Pesticide | % Active | Disintegration | Breakup | Rating |
|---|---|---|---|---|---|
| Celite 500 | Mancozeb (DG) | 20 | 6 | 4 | Fair |
| Celite 500 | Mancozeb (DG) | 30 | 5 | 3 | Fair |
| Celite 500 | Mancozeb (Dithane) | 15 | 7 | 6 | Good |
| Celite 500 | Mancozeb (Dithane) | 30 | 6 | 5 | Fair |
| Celite 500 | Chlorothalanil | 2 | 8 | 8 | Good |

EXAMPLE 12

It is also an embodiment of this invention to incorporate multiple pesticidal products into the dry spreadable granules. This can be accomplished in several ways, for example: 1) blending two or more pesticides in the starting material of the homogeneous process; 2) spraying two or more pesticides upon the diatomaceous earth-surfactant granules as in the spray-on process described above; or 3) a combination of these processes, that is, incorporating one or more pesticides in a homogeneous process followed by the spraying of one or more pesticides upon the homogeneously prepared granules.

Dry spreadable granules containing two pesticides are prepared in accordance with the homogeneous process of Example 5. The weight percentages of the two pesticides; their identities and the performance results of the final granulated products are set forth in Table XII below.

TABLE XII

| Sample | Pesticides | Ingredient Percentages | Disintegration | Breakup | Rating |
|---|---|---|---|---|---|
| Celite 500 | Chlorothalanil, Iprodione | 3%/1.5% | 8 | 8 | Good |
| Celite 500 | Chlorothalanil, Iprodione | 4%/1% | 7 | 7 | Good |
| Celite 500 | Chlorothalanil, Iprodione | 8%/2% | 7 | 7 | Good |
| Celite 500 | Chlorothalanil, Iprodione | 12%/3% | 7 | 6 | Good |

EXAMPLE 13

A series of homogeneously processed granules are produced as set forth in Example 5 using a 1.0 mm or a 2.0 mm die on the extruder to determine the effect of particle size on Disintegration performance. The resulting data are indicated in Table XIII below.

TABLE XIII

| Sample | % Active | Disintegration (1.0 mm) | Disintegration (2.0 mm) |
|---|---|---|---|
| Oxadiazon | 2 | 8 | 6 |
| Fosetyl Al | 1.6 | 8 | 7 |
| Iprodione | 2.5 | 8 | 8 |

EXAMPLES 14–17

Two formulations of dry spreadable granules are prepared according to the spray process of this invention as set forth in Example 6. One formulation (Chlor 2 SDSG) is composed of:

2.0 wt % Chlorpyrifos
3.0 wt % Supragil WP
4.0 wt % Soprophor S/40-P
8.0 wt % Supragil MNS/90
83.0 wt % Diatomaceous Earth (Celite 500)

The other formulation (Chlor 3 SDSG) is composed of:

3.0 wt % Chlorpyrifos
3.0 wt % Supragil WP
4.0 wt % Soprophor S/40-P
8.0 wt % Supragil MNS/90
82.0 wt % Diatomaceous Earth (Celite 500)

Using the above prepared dry spreadable granules, field trials are conducted in Georgia, USA using replicated field plots. The formulations are applied as indicated below at 1.0, 2.0, and 3.0 pounds of active ingredient per acre (lb ai/ac) and compared to a commercial dry spreadable granular chlorpyrifos formulation of the Dow Chemical Company, i. e., Dursban 2G, applied at the same rates.

Relative insect damage ratings, in the case of the Mole Crickets, or the number of live grubs, in the case of the Southern Masked Chafer grubs, are determined prior to the treatment application and subsequently at 1–2 week intervals. The granules are applied with standard research plot broadcasting equipment.

The detailed results of the trials together with a discussion of the realizable effects are set forth below. The first field trials are with the Early Season Mole Cricket and are conducted at the Sea Island Golf Club on St Simons Island. The results of these trials are as indicated in Table XIV.

TABLE XIV

Efficacy of Chlor SDSG Formulations on Early Season Control of Mole Crickets (St. Simons Island, GA)

| | PRE* | 1WAT** | 2WAT | 4WAT | 6WAT | 8WAT |
|---|---|---|---|---|---|---|
| Chlor 2SDSG 1.0 lb ai/ac | 3.47 | 2.72 | 2.9 | 3.5 | 3.3 | |
| Chlor 2SDSG 2.0 lb ai/ac | 3.45 | 1.72 | 1.675 | 2.32 | 1.67 | 2.55 |
| Chlor 2SDSG 3.0 lb ai/ac | 3.9 | 1.03 | 0.925 | 0.88 | 0.88 | 1.4 |
| Chlor 3SDSG 2.0 lb ai/ac | 3.72 | 1.52 | 1.2 | 1.73 | 1.33 | 2.47 |
| Chlor 3SDSG 3.0 lb ai/ac | 3.6 | 0.82 | 0.675 | 0.9 | 0.95 | 1.63 |
| Dursban 2G 1.0 lb ai/ac | 3.6 | 2.63 | 3.05 | 3.45 | 3.55 | |
| Dursban 2G 2.0 lb ai/ac | 3.55 | 2.08 | 1.9 | 2.97 | 2.47 | 4.15 |
| Dursban 2G 3.0 lb ai/ac | 3.63 | 1.75 | 1.575 | 1.93 | 1.35 | 3.53 |
| Control | 3.45 | 3.5 | 3.5 | 4.38 | 5.78 | |

*PRE = Before Treatment
**WAT = Weeks After Treatment

Each of the above formulations reduces the Mole Cricket damage as compared to the Control and as the treatment rate increases, damage decreases. Damage is excessive for the Control and 1.0 lb ai/ac treatments by 8 weeks after the application and so no damage ratings are indicated for these conditions at that time.

Most significant in this trial is the efficacy of the dry spreadable granules of this invention. At rates of 2 lb ai/ac or greater, efficacy is consistently superior to that of the same rate of the commercial dry spreadable chlorpyrifos formulation. The two broadcast granule formulations of this invention, i. e., the 2 wt % and 3 wt %, when applied at 2.0 lb ai/ac, are as effective as the 3.0 lb ai/ac rate of the commercial granular product and therefore are obviously more efficacious than current commercially acceptable dry spreadable granular formulations. Note that in the 3 wt % ai dry spreadable granules of this invention, the efficacy is superior to the commercial dry spreadable granular product even though the amount of the formulated product of this invention applied per plot is one-third less than the commercial material application amount.

The second field trials are with Late Instar Mole Cricket Nymphs and Adults and are conducted at The Links at Cabin Bluff in St. Marys, Ga. and also at the St. Simons Island Club on St. Simons Island, Ga. The results of these trials are as indicated in Tables XV and XVI respectively.

TABLE XV

Efficacy of Chlor SDSG Formulations on Late Instar Nymphs and Adult Mole Crickets (St. Marys, GA)

|  | PRE* | 1WAT** | 2WAT | 4WAT | 6WAT |
|---|---|---|---|---|---|
| Chlor 2SDSG 2.0 lb ai/ac | 4.27 | 1.27 | 0.9 | 0.87 | 1.07 |
| Chlor 2SDSG 3.0 lb ai/ac | 4.3 | 1.07 | 0.5 | 0.57 | 0.9 |
| Chlor 3SDSG 2.0 lb ai/ac | 4.0 | 2.07 | 1.73 | 1.27 | 1.23 |
| Chlor 3SDSG 3.0 lb ai/ac | 3.4 | 2.03 | 1.77 | 1.17 | 1.13 |
| Dursban 2G 2.0 lb ai/ac | 3.63 | 2.1 | 2.2 | 1.93 | 2.2 |
| Dursban 2G 3.0 lb ai/ac | 3.9 | 1.67 | 1.5 | 1.17 | 1.23 |
| Control | 3.7 | 5.63 | 6.7 | 7.2 | 7.17 |

*PRE = Before Treatment
**WAT = Weeks After Treatment

At these field trials, while every formulation reduces Mole Cricket damage as compared to the Control (no treatment), all of the dry spreadable granules of this invention outperformed the commercial Dursban 2G formulation applications at both the 2 and 3 lb ai/ac rates.

The two dry spreadable granular formulations of this invention, i. e., the 2% and 3% ai, when applied at 2.0 lb ai/ac are significantly more effective than even the 3.0 lb ai/ac rate of the commercial granular formulation. Even application of reduced volumes of 3% formulated product of this invention does not result in a significant deleterious reduction in performance. In these trials, the 2% ai formulations of this invention perform better than the 3% granules.

TABLE XVI

Efficacy of Chlor SDSG Formulations on Late Instar Nymphs and Adult Mole Crickets (St. Simons, GA)

|  | PRE* | 1WAT** | 2WAT | 4WAT | 6WAT |
|---|---|---|---|---|---|
| Chlor 2SDSG 2.0 lb ai/ac | 3.43 | 1.53 | 1.77 | 1.333 | 0.73 |
| Chlor 2SDSG 3.0 lb ai/ac | 4.27 | 0.87 | 1.07 | 0.7 | 0.67 |
| Chlor 3SDSG 2.0 lb ai/ac | 4.1 | 2.33 | 2.63 | 1.933 | 1.27 |
| Chlor 3SDSG 3.0 lb ai/ac | 3.73 | 1.93 | 2.27 | 1.733 | 1.23 |
| Dursban 2G 2.0 lb ai/ac | 4.1 | 2.57 | 3.2 | 2.0 | 1.7 |
| Dursban 2G 3.0 lb ai/ac | 3.87 | 1.37 | 1.97 | 1.5 | 0.93 |
| Control | 3.9 | 5.27 | 6.03 | 7.233 | 8.73 |

*PRE = Before Treatment
**WAT = Weeks After Treatment

The third set of field trials at St. Simons on the Late Instar Nymphs and Adult Mole Crickets as set forth in Table XVI are similar to that achieved at the St. Marys field trials. The 2% dry spreadable granules of the instant invention significantly outperform the 2% Dursban commercial granules in similar applications conditions.

TABLE XVII

Efficacy of Chlor SDSG Formulations on Southern Masked Chafer (St. Simons Island, GA)

|  | PRE | 1WAT | 2WAT | 3WAT | 5WAT |
|---|---|---|---|---|---|
| chlor 2SDSG 3.0 lb ai/ac | 44.07 | 29.0 | 26.83 | 27.67 | 25.00 |
| Chlor 3SDSG 3.0 lb ai/ac | 52.73 | 27.87 | 27.97 | 26.37 | 26.83 |
| Dursban 2G 3.0 lb ai/ac | 40.3 | 36.17 | 30.17 | 40.33 | 33.93 |
| Control | 46.33 | 43.5 | 42.57 | 44.6 | 42.57 |

*PRE = Before Treatment
**WAT = Weeks After Treatment

At treatment rates of 3.0 lb ai/ac, the dry spreadable granular formulations of this invention provide significant improvements in grub control over similar applications utilizing the commercial Dursban 2G formulations. Improved control is observed even when the amount of formulated product applied is reduced by one-third.

Thus, in the field trials, the chlorpyrifos dry spreadable granule formulations of this invention outperform commercial Dursban 2G granular formulations for control of all stages of Mole Crickets and the Southern Masked Chafer in southern turf. This exceptional performance is obtained with both 2% and 3% ai granule loadings. Improved control is obtained even when the quantity of formulated granular product applied per acre is significantly reduced.

In conclusion, the above trials indicate that the dry spreadable granular formulations-of this invention can significantly enhance control of soil-borne pests, pathogens, and weeds while concomitantly reducing pesticide application rates, worker exposure to applied and potentially toxic materials, and the overall pesticide load in the environment.

EXAMPLE XVIII

A series of four tests were run to compare two of the dry spreadable granules of the instant invention, i.e., 2% and 3% chlorpyrifos granules prepared as in Example 5, against a number of commercial water-dispersible granules as identified below. The four tests performed on each of the compositions were as follows: the Disintegration test; the Breakup test, a measurement of the "% Fines" which reflects the percentage of the dry material which passes through a 20 mesh screen, and a "% Suspensibility" test.

The "% Suspensibility" test is a standard ASTM procedure in which 4 grams of product is poured at room temperature into 50 ml of water, stirred for 2 minutes, poured into a 250 ml graduated cylinder which is then filled with water and inverted 10 times. The column is allowed to sit for 30 minutes; the top 225 ml is vacuumed off; and the remaining 25 ml placed in a 50° C. oven until a constant weight is attained. The percentage of the material in the 25 ml sample is determined and the amount suspended by difference. The results are set forth in Table XVIII below.

TABLE XVIII

| | % Suspensibility | Disintegration Value | Breakup | % Fines |
|---|---|---|---|---|
| Sencor DF (TM Mobay Corp.) | 65.55 | 6 | 3 | 16.9 |
| BAYLETON (TM Mobay Corp.) | 92.5 | 4 | 4 | 22.3 |
| PURSUIT 70 DG (TM Am. Cyan.) | 66.67 | 4 | 3 | 1.9 |
| Atrazine 90 DF (TM Ciba Geigy) | 91.67 | 2 | 4.5 | 7.5 |
| SYNCHRONY STS (DuPont) | 89.17 | 3 | 3 | 68.6 |
| KARMEX DF (DuPont) | 80 | 2 | 4.5 | 22.2 |
| 2% Chlorpyrifos SWDG | 29.44 | 6.5 | 7 | 2.78 |
| 3% Chlorpyrifos SWDG | 31.11 | 6 | 6.5 | 7.11 |

From the above results, it can be observed that the commercial water-dispersible granules perform better in terms of "% Suspensibility" than the broadcast granules of the instant invention, but give a poorer performance in the Disintegration and Breakup tests.

Viewed another way, commercial water-dispersible granules can give better suspension characteristics when subject to mechanical agitation than the broadcast granules of this invention. However, the dry spreadable granules of this invention give better disintegration and breakup, i.e., spreadability in the absence of agitation. In addition, most of the commercial water-dispersible granules have much larger amounts of fines than the instant granules and thus present a higher respiratory hazard.

The above results clearly set forth that the granules of this invention significantly outperform commercial water-dispersible granules in direct broadcast agricultural applications.

Although the invention is described with respect to specific modifications, the details thereof are not to be construed as limitations except to the extent indicated in the following claims.

What is claimed is:

1. A method of delivery of a bioactive compound to a site to be treated comprising the steps of:
   A) broadcasting upon the site a bioactively effective amount of a dry spreadable granular composition comprising:
   a) from 35 to 95 weight percent of diatomaceous earth having an internal surface area in the range of from greater than about 5 to less than about 90 square meters per gram and a pore volume in the range of from greater than about 2 to less than about 5 cubic centimeters per gram;
   b) from 5 to 40 weight percent of a surfactant composition comprising:
      i) from 3 to 15 weight percent of a polymeric anionic surfactant disintegration aid;
      ii) from 2 to 15 weight percent of a non-polymeric anionic surfactant rewetting agent; and
      iii) from 2 to 6 weight percent of a binder selected from the group consisting of alkanolamides, ethylene bisamides, fatty acid esters, glycerol esters, sorbitan esters, alkylphenol ethoxylates, alcohol alkoxylates, tristyrylphenol ethoxylates, mercaptan ethoxylates, end-capped block copolymers, ethylene oxide/propylene oxide (EO/PO) block copolymers, tetra functional (EO/PO) block copolymers, and mixtures thereof; and
   c) from 0.005 to 30 weight percent of a bioactive compound;
   wherein the weight percents are based on the total weight of the dry spreadable granular composition and said granular composition, in a granule size of 2 mm, has a Disintegration value and a Breakup value of from 6 to 9; and
   B) subsequently contacting said dry spreadable granular composition with water.

2. The method of claim 1 wherein the anionic surfactants are individually and independently selected from the group consisting of:
   i) alkyl and alkyl ether sulfates;
   ii) water soluble salts of the formula:

$R_1-SO_3-M$ wherein M is a water-soluble cation, and $R_1$ is selected from the group consisting of
      a) a straight or branched chain, saturated aliphatic hydrocarbon radical having from 8 to 24 carbon atoms;
      b) a mono-, di-, or tri- $C_1-C_6$ alkyl substituted aryl;
      c) alpha-olefins having 12 to 24 carbon atoms; and
      d) naphthalene-formaldehyde condensation products;
   iii) isethionates;
   iv) N-methyl taurates;
   v) sulfosuccinates;
   vi) sulfosuccinamates;
   vii) B-alkoxy alkane sulfonates;
   viii) disulfonates;
   ix) alkali or alkali earth metal salts of lignosulfonates;
   x) ethoxylated derivatives of the above-identified anionic surfactants; and
   xi) mixtures thereof.

3. The method of claim 1 wherein the diatomaceous earth has an internal surface area in the range of from greater than about 10 to less than about 60 square meters per gram and a pore volume in the range of from greater than about 3 to less than about 4 cubic centimeters per gram.

4. The method of claim 1 wherein the surfactant composition binder comprises ethylene oxide/propylene oxide block copolymer.

5. The method of claim 1 wherein the bioactive compound is a pesticide.

6. The method of claim 5 wherein the pesticide is an insecticide.

7. The method of claim 1 wherein the bioactive compound is a fertilizer.

8. A method of delivery of a bioactive compound to a site to be treated comprising the steps of:
   A) broadcasting upon the site a bioactively effective amount of a dry spreadable granular composition comprising:
   a) from 35 to 95 weight percent of diatomaceous earth having an internal surface area in the range of from greater than about 5 to less than about 90 square meters per gram and a pore volume in the range of from greater than about 2 to less than about 5 cubic centimeters per gram;
b) from about 5 to 40 weight percent of a surfactant composition comprising:
  i) from 3 to 10 weight percent of a water soluble salt of an alkylnaphthalene-sulfonate-formaldehyde condensate;
  ii) from 1 to 5 weight percent alkylnaphthalene-sulfonate; and
  iii) from 1 to 5 weight percent tristyrylphenol ethoxylate; and
c) from 0.005 to 30 weight percent of a bioactive compound; wherein the weight percents are based on the total weight of the dry spreadable granular composition and said granular composition, in a granule size of 2 mm, has a Disintegration value and a Breakup value of from 6 to 9; and
B) subsequently contacting said dry spreadable granular composition with water.

* * * * *